(12) United States Patent
Ogura et al.

(10) Patent No.: US 6,808,497 B2
(45) Date of Patent: Oct. 26, 2004

(54) BLOOD-PRESSURE MEASURING APPARATUS AND INFERIOR-AND-SUPERIOR-LIMB BLOOD-PRESSURE-INDEX MEASURING APPARATUS

(75) Inventors: Toshihiko Ogura, Komaki (JP); Tomohiro Nunome, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 50 days.

(21) Appl. No.: 10/265,388

(22) Filed: Oct. 7, 2002

(65) Prior Publication Data

US 2003/0163053 A1 Aug. 28, 2003

(30) Foreign Application Priority Data

Feb. 26, 2002 (JP) .................................. 2002-049865

(51) Int. Cl.[7] ................................................ A61B 5/02
(52) U.S. Cl. ...................... 600/490; 600/492; 600/549; 600/301
(58) Field of Search ................................ 600/481, 483, 600/485, 490–497, 500–503, 549, 301, 499

(56) References Cited

U.S. PATENT DOCUMENTS

| 4,397,317 | A | 8/1983 | Villa-Real |
| 4,429,700 | A | 2/1984 | Thees et al. |
| 5,255,686 | A | * 10/1993 | Takeda et al. ............... 600/494 |
| 2001/0047126 | A1 | 11/2001 | Nagai et al. |

FOREIGN PATENT DOCUMENTS

| EP | 0 377 554 A1 | 7/1990 | |
| EP | 377554 A1 | * 7/1990 | ........... A61B/5/022 |
| EP | 1 050 267 A1 | 11/2000 | |
| JP | A 3-231629 | 10/1991 | |
| JP | 03231629 A | * 10/1991 | ........... A61B/5/022 |
| JP | A 7-116131 | 5/1995 | |

OTHER PUBLICATIONS

JP 03231629 A, Fukuyoshi et al, Hemodynamometer, Oct. 15, 1994 (Translation).*
EP 377554 A1, Schauer, Device For Measuring Blood Pressure, Jul. 11, 1990 (Translation).*

* cited by examiner

Primary Examiner—Mary Beth Jones
Assistant Examiner—Navin Natnithithadha
(74) Attorney, Agent, or Firm—Oliff & Berridge, PLC

(57) ABSTRACT

An apparatus for measuring a blood pressure of a living subject, including an inflatable cuff which has an inside surface adapted to contact a body surface of the subject and an outside surface exposed to an ambient air, and which is adapted to be wound around a portion of the subject to press the portion of the subject, a temperature sensor which is provided in the inside surface of the cuff and detects, in a state in which the cuff is wound around the portion of the subject, a temperature of the portion of the subject, and a display device which displays the temperature of the portion of the subject detected by the first temperature sensor.

7 Claims, 4 Drawing Sheets

BLOOD-PRESSURE MEASURING APPARATUS AND INFERIOR-AND-SUPERIOR-LIMB BLOOD-PRESSURE-INDEX MEASURING APPARATUS

BACKGROUND OF THE INVENTION

1. Field of the Invention

The present invention relates to a blood-pressure measuring apparatus which measures a blood pressure of a living subject, and an inferior-and-superior-limb blood-pressure-index measuring apparatus which measures an inferior-and-superior-limb blood-pressure index of a living subject.

2. Related Art Statement

A blood pressure of a living subject can be measured using an inflatable cuff which is wound around a portion of the subject, such as an upper or an ankle. For example, there are known a Korotkoff-sound blood-pressure measuring apparatus which determines, as a systolic and a diastolic blood pressure of a living subject, respective pressures of a cuff at respective times when the first and last Korotkoff sounds occur during decreasing of the cuff pressure, and an oscillometric blood-pressure measuring apparatus which determines a systolic and a diastolic blood pressure of a living subject, based on change of respective amplitudes of respective pulses of a pulse wave detected during changing of pressure of a cuff.

Meanwhile, a body temperature of a peripheral portion of a living subject is lower than that of a central portion of the same. Therefore, an artery of the peripheral portion of the subject more contracts than that of the central portion of the same, under influence of the lower body temperature. Thus, when a blood pressure of the subject is measured using a cuff that is wound around the peripheral portion, the accuracy of measurement of the blood pressure is not so high. In particular, when an inferior-and-superior-limb blood-pressure index, i.e., the ratio of a superior-limb blood pressure to an inferior-limb blood pressure or the ratio of an inferior-limb blood pressure to a superior-limb blood pressure is measured to diagnose arteriostenosis, a cuff is wound around, e.g. an ankle to measure a blood pressure of the ankle. Thus, the accuracy of measurement of the ankle blood pressure or the inferior-and-superior-limb blood-pressure index obtained therefrom may be lowered by the influence of temperature of the ankle or the leg.

SUMMARY OF THE INVENTION

It is therefore an object of the present invention to provide a blood-pressure measuring apparatus or an inferior-and-superior-limb blood-pressure-index measuring apparatus that can measure a reliable blood pressure of a living subject even when a cuff is worn on a peripheral portion of the subject.

The above object has been achieved by the present invention. According to a first aspect of the present invention, there is provided an apparatus for measuring a blood pressure of a living subject, comprising an inflatable cuff which has an inside surface adapted to contact a body surface of the subject and an outside surface exposed to an ambient air, and which is adapted to be wound around a portion of the subject to press the portion of the subject; a first temperature sensor which is provided in the inside surface of the cuff and detects, in a state in which the cuff is wound around the portion of the subject, a temperature of the portion of the subject; and a display device which displays the temperature of the portion of the subject, detected by the first temperature sensor.

According to this aspect, the first temperature sensor is provided in the inside surface of the cuff wound around the portion of the living subject, and the display device displays the temperature of the portion of the subject detected by the first temperature sensor. Since an operator such as a doctor can recognize the temperature of the portion of the subject around which the cuff used for the measurement of blood pressure is wound, the operator can easily judge whether the blood pressure measured using the cuff is reliable or not. If the temperature of the portion of the subject displayed by the display device falls within a pre-determined normal range, the operator can judge that the measured blood pressure is not lowered by the influence of the body temperature. On the other hand, if the temperature of the portion of the subject displayed by the display device does not fall within the normal range, the operator can again operate the present apparatus to obtain a reliable blood-pressure value of the subject.

According to a preferred feature of the first aspect of the present invention, the blood-pressure measuring apparatus further comprises a second temperature sensor which is provided in the outside surface of the cuff and detects, in the state in which the cuff is wound around the portion of the subject, a temperature of the ambient air, and the display device additionally displays the temperature of the ambient air, detected by the second temperature sensor.

According to this feature, the display device displays the temperature of the portion of the subject around which the cuff is wound and additionally displays the temperature of the ambient air. Therefore, if the temperature of the portion of the subject is low, the operator can easily judge whether the temperature of the portion is lowered because of the influence of the temperature of the ambient air, e.g., room temperature.

According to another feature of the first aspect of the present invention, the blood-pressure measuring apparatus further comprises a temperature-difference determining means for determining a difference between the temperature of the portion of the subject detected by the first temperature sensor and the temperature of the ambient air detected by the second temperature sensor, and the display device additionally displays the temperature difference determined by the temperature-difference determining means.

According to this feature, the operator can easily recognize the temperature difference between the temperature of the portion of the subject around which the cuff is wound and the temperature of the ambient air. Therefore, if the temperature of the portion of the subject is low, the operator can easily take a treatment or an action against the low temperature. More specifically described, if the temperature of the portion of the subject is low and the above-indicated temperature difference is considerably small, the operator can raise the room temperature; and if the temperature of the portion of the subject is low and the temperature difference is considerably large, the operator can positively raise the temperature of the portion of the subject by wearing a cloth on the portion or giving a massage to the portion.

According to another feature of the first aspect of the present invention, the blood-pressure measuring apparatus further comprises a judging means for judging whether the temperature difference determined by the temperature-difference determining means is greater than a reference value; and an output device which outputs information indicating a judgment made by the judging means.

According to this feature, the output device outputs the information, such as a message in the form of a sound or an image, or a printed matter. From the information, the operator can easily recognize the temperature difference between the temperature of the portion of the subject around which the cuff is wound and the temperature of the ambient air. Therefore, if the temperature of the portion of the subject is low, the operator can easily take a treatment or an action against the low temperature.

According to a second aspect of the present invention, there is provided an apparatus for measuring an inferior-and-superior-limb blood-pressure index of a living subject, comprising an inferior-limb blood-pressure measuring device which includes an inferior-limb cuff adapted to be wound around an inferior limb of the subject and measures a blood pressure of the inferior limb; a superior-limb blood-pressure measuring device which includes a superior-limb cuff adapted to be wound around a superior limb of the subject and measures a blood pressure of the superior limb; an inferior-and-superior-limb blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device; a display device which displays the inferior-and-superior-limb blood-pressure index of the subject determined by the inferior-and-superior-limb blood-pressure-index determining means; an inferior-limb temperature measuring device which measures a temperature of the inferior limb of the subject; a superior-limb temperature measuring device which measures a temperature of the superior limb of the subject; and a display control means for controlling the display device to simultaneously display the temperature of the inferior limb of the subject measured by the inferior-limb temperature measuring device and the temperature of the superior limb of the subject measured by the superior-limb temperature measuring device.

According to this aspect, the display control means controls the display device to simultaneously display the temperature of the inferior limb of the subject measured by the inferior-limb temperature measuring device and the temperature of the superior limb of the subject measured by the superior-limb temperature measuring device. Since the operator can recognize the respective temperatures of the superior and inferior limbs around which the respective cuffs are wound for the blood-pressure measurement, the operator can easily judge whether the respective blood-pressure values measured by the superior-limb blood-pressure measuring device and the inferior-limb blood-pressure measuring device are reliable. For example, if the temperature of the inferior limb is much lower than that of the superior limb, the operator can judge that the accuracy of the blood pressure of the inferior limb is low because of the influence of the low temperature of the inferior limb. In this case, the operator can try to measure a reliable blood-pressure value after raising the temperature of the inferior limb.

According to a third aspect of the present invention, there is provided an apparatus for measuring an inferior-and-superior-limb blood-pressure index of a living subject, comprising an inferior-limb blood-pressure measuring device which includes an inferior-limb cuff adapted to be wound around an inferior limb of the subject and measures a blood pressure of the inferior limb; a superior-limb blood-pressure measuring device which includes a superior-limb cuff adapted to be wound around a superior limb of the subject and measures a blood pressure of the superior limb; an inferior-and-superior-limb blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device; a display device which displays the inferior-and-superior-limb blood-pressure index of the subject determined by the inferior-and-superior-limb blood-pressure-index determining means; an inferior-limb temperature measuring device which measures a temperature of the inferior limb of the subject; a superior-limb temperature measuring device which measures a temperature of the superior limb of the subject; a temperature-difference determining means for determining a difference between the temperature of the inferior limb of the subject measured by the inferior-limb temperature measuring device and the temperature of the superior limb of the subject measured by the superior-limb temperature measuring device; and an output device which outputs, when the temperature difference determined by the temperature-difference determining means is greater than a reference value, information related to a fact that the temperature difference is greater than the reference value.

According to this aspect, if the difference between the respective temperatures of the inferior and superior limbs, determined by the temperature-difference determining means, is greater than the reference value, the output device outputs information related to a fact that the temperature difference is greater than the reference value. Thus, the operator can easily judge whether the respective blood-pressure values measured by the superior-limb blood-pressure measuring device and the inferior-limb blood-pressure measuring device are reliable. For example, if the temperature of the inferior limb is much lower than that of the superior limb, the operator can judge that the accuracy of the blood pressure of the inferior limb is low because of the influence of the low temperature of the inferior limb. In this case, the operator can try to measure a reliable blood-pressure value after raising the temperature of the inferior limb.

According to a preferred feature of the second or third aspect of the present invention, the inferior-limb temperature measuring device comprises an inferior-limb temperature sensor which is provided in an inside surface of the inferior-limb cuff and is adapted to contact a skin of the inferior limb of the subject so as to measure the temperature of the inferior limb of the subject.

According to this feature, when the inferior-limb cuff is worn on the inferior limb, the inferior-limb temperature sensor is simultaneously worn on the inferior limb to measure the temperature of the inferior limb.

According to another feature of the second or third aspect of the present invention, the inferior-and-superior-limb blood-pressure-index measuring apparatus further comprises an ambient-air temperature sensor which is provided in an outside surface of the inferior-limb cuff and detects, in the state in which the inferior-limb cuff is wound around the inferior limb of the subject, a temperature of the ambient air.

According to this feature, when the inferior-limb cuff is worn on the inferior limb, the ambient-air temperature sensor is simultaneously worn on the inferior limb to measure the temperature of the ambient air.

According to another feature of the second or third aspect of the present invention, the superior-limb temperature measuring device comprises a superior-limb temperature sensor which is provided in an inside surface of the superior-limb cuff and is adapted to contact a skin of the superior limb of the subject so as to measure the temperature of the superior limb of the subject.

According to this feature, when the superior-limb cuff is worn on the superior limb, the superior-limb temperature sensor is simultaneously worn on the superior limb to measure the temperature of the superior limb.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Hereinafter, there will be described a preferred embodiment of the present invention in detail by reference to the drawings.

Figure 1:
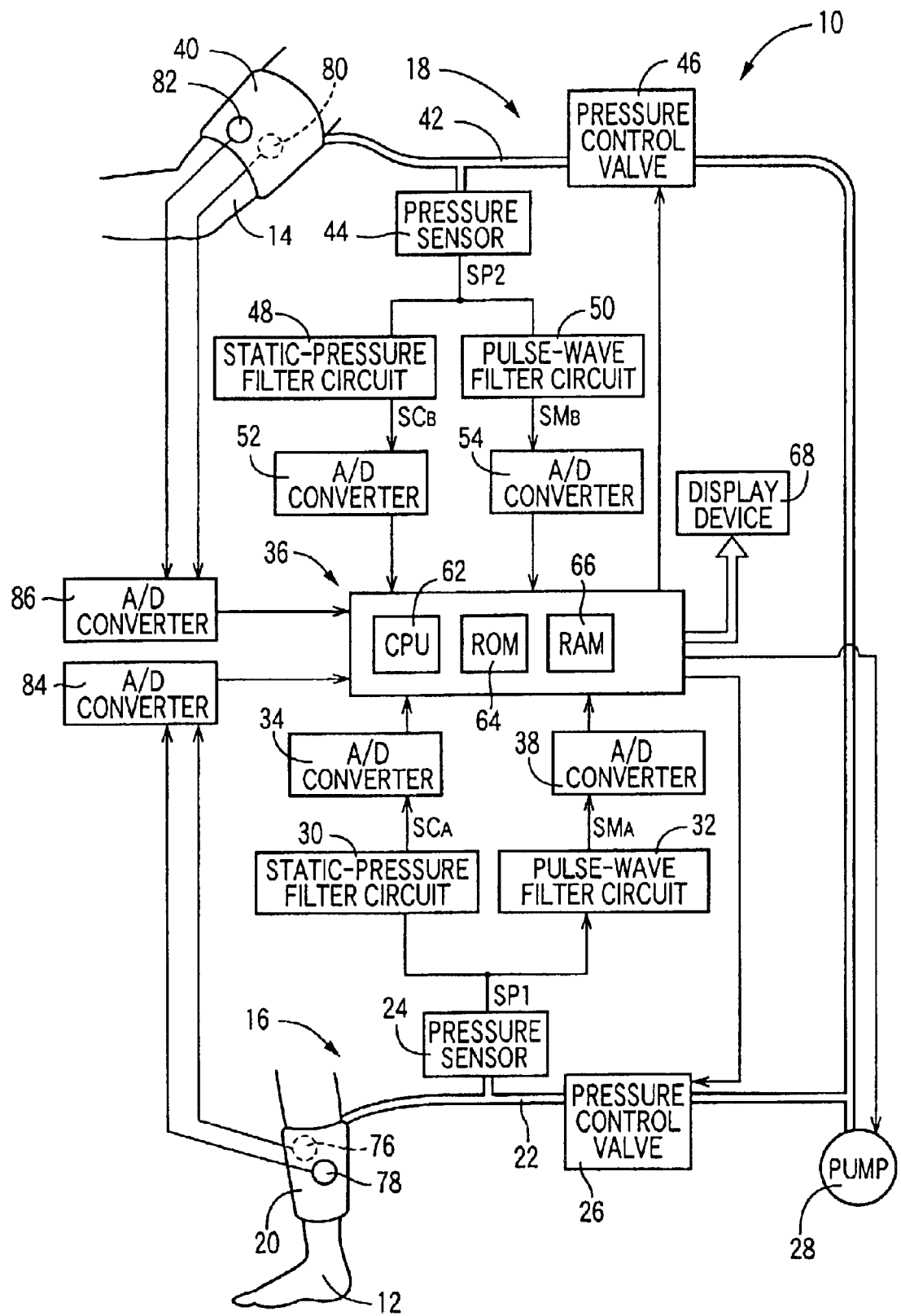
FIG. 1 is a diagrammatic view for explaining a construction of an ankle-and-upper-arm blood-pressure-index measuring apparatus to which the present invention is applied.

FIG. 1 is a diagrammatic view for explaining a construction of an ankle-and-upper-arm blood-pressure-index measuring apparatus 10 to which the present invention is applied. The ankle-and-upper-arm blood-pressure-index measuring apparatus 10, shown in FIG. 1, functions as an inferior-and-superior-limb blood-pressure-index measuring apparatus wherein an ankle 12 is selected as an inferior limb and an upper arm 14 is selected as a superior limb. The present apparatus 10 carries out measurements on a patient as a living subject who takes a face-up, a lateral, or a face-down position so that the upper arm and ankle of the patient are substantially level with each other.

FIG. 1, the ankle-and-upper-arm blood-pressure index measuring apparatus 10 includes an ankle blood-pressure measuring device 16 which measures a blood-pressure value of the ankle 12 and which functions as an inferior-limb blood-pressure measuring device, and an upper-arm blood-pressure measuring device 18 which measures a blood-pressure value of the upper arm 14 and functions as a superior-limb blood-pressure measuring device.

The ankle blood-pressure measuring device 16 includes an ankle cuff 20 which includes a belt-like cloth bag and a rubber bag accommodated in the cloth bag and which is adapted to be wound around the ankle 12 of the patient; a piping 22; and a pressure sensor 24, a pressure control valve 26, and an air pump 28 which are connect to the ankle cuff 20 via the piping 22. The pressure control valve 26 adjusts a pressure of a ressurized air supplied from the air pump 28, and supplies the pressure-adjusted air to thee cuff 20, or discharges the pressurized air from the ankle cuff 20, so as to control an air pressure in the ankle cuff 20.

The pressure sensor 24 detects the air pressure in the ankle cuff 20, and supplies a pressure signal, SP1, representing the detected air pressure, to a static-pressure filter circuit 30 and a pulse-wave filter circuit 32. The static-pressure filter circuit 30 includes a low-pass filter which extracts, from the pressure signal SP1, an ankle-cuff-pressure signal, $SC_A$, representing a static component of the detected air pressure, i.e., a pressing pressure of the ankle cuff 20 (hereinafter, referred to as the ankle-cuff pressure, $PC_A$). The filter circuit 30 supplies the ankle-cuff-pressure signal $SC_A$ to an electronic control device 36 via an A/D (analog-to-digital) converter 34.

The pulse-wave filter circuit 32 includes a band-pass filter which extracts, from the pressure signal SP1, an ankle-pulse-wave signal, $SM_A$, representing an ankle pulse wave as an oscillatory component of the detected air pressure that has prescribed frequencies. The filter circuit 32 supplies the ankle-pulse-wave signal $SM_A$ to the control device 36 via an A/D converter 38. Since the ankle pulse wave indicates the oscillation of pressure of the ankle cuff 20, the filter circuit 32 functions as an ankle-pulse-wave detecting device.

The upper-arm blood-pressure measuring device 18 includes an upper-arm cuff 40 having a construction identical with that of the cuff of the ankle blood-pressure measuring device 16; and a piping 42, a pressure sensor 44, and a pressure control valve 46. The upper-arm cuff 40 is wound around the upper arm 14. The pressure control valve 46 is connected to the air pump 28. The pressure sensor 44 detects an air pressure in the upper-arm cuff 40, and supplies a pressure signal, SP2, representing the detected air pressure, to a static-pressure filter circuit 48 and a pulse-wave filter circuit 50 which have respective constructions identical with those of the counterparts of the ankle blood-pressure measuring device 16. The static-pressure filter circuit 48 extracts, from the pressure signal SP2, an upper-arm-cuff-pressure signal, $SC_B$, representing a static component of the detected air pressure, i.e., a pressing pressure of the upper-arm cuff 40 (hereinafter, referred to as the upper-arm-cuff pressure, $PC_B$). The filter circuit 48 supplies the upper-arm-cuff-pressure signal $SC_B$ to the control device 36 via an A/D converter 52. The pulse-wave filter circuit 50 extracts, from the pressure signal SP2, an upper-arm-pulse-wave signal, $SM_B$, representing an upper-arm pulse wave as an oscillatory component of the detected air pressure that has prescribed frequencies. The filter circuit 50 supplies the upper-arm-pulse-wave signal $SM_B$ to the control device 36 via an A/D converter 54. Since the upper-arm pulse wave indicates the oscillation of pressure of the upper-arm cuff 40, the filter circuit 50 functions as an upper-arm-pulse-wave detecting device.

The control device 36 is essentially provided by a microcomputer including a CPU (central processing unit) 62, a ROM (read only memory) 64, a RAM (random access memory) 66, and an I/O (input-and-output) port, not shown, and the CP 62 processes signals according to the programs pre-stored in the ROM 64, while utilizing the data-storing function of the RAM 66. The control device 36 outputs, from the I/O port, drive signals to the air pump 28 and the two pressure control valves 26, 46 so as to control the respective operations thereof and thereby control the respective air pressures of the ankle cuff 20 and the upper-arm cuff 40. In addition, the CPU 62 processes signals supplied to th control device 36, so as to determine an ankle-and-upper-arm blood-pressure index (or Ankle Arm Blood-Pressure Index; hereinafter, referred to as an ABI value) and evaluation information, and control a display device 68 to display the thus determined ABI value and evaluation information.

Figure 2:
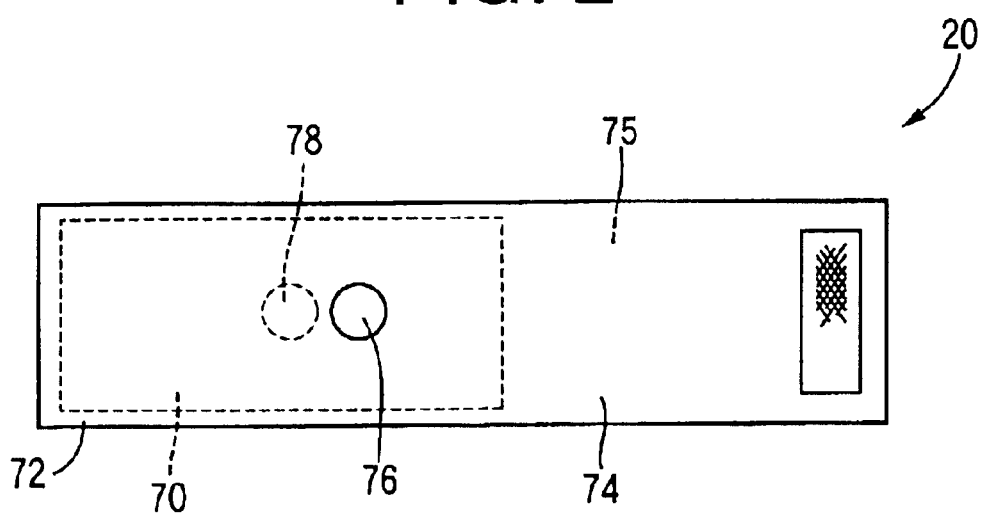
FIG. 2 is a view of an ankle cuff, shown in FIG. 1, that is unfolded to show an inside surface thereof.

The belt-like ankle cuff 20 supports a temperature sensor 76 on an inside surface 74 that is adapted to contact a body surface of the subject in the state in which the cuff 20 is wound around the ankle 12; and a temperature sensor 76 on an outside surface 75 that is exposed to an ambient air in the state in which the cuff 20 is wound around the ankle 12. As shown in FIG. 2, the ankle cuff 20 includes an elongate bag 72 formed of a non-stretchable cloth and an inflatable rubber bag 70 accommodated in the elongate bag 72. In a state in which the ankle cuff 20 is wound around the ankle 12 as a portion of the subject, a fastener sheet provided on the inside surface 74 of one end portion of the ankle cuff 20 is fastened to a fastener sheet provided on the outside surface 75. The temperature sensor 76 is a body-temperature sensor that is exclusively used to measure a temperature of the subject's portion around which the ankle cuff 20 is wound. Since this temperature sensor 76 measures a temperature in a state in which the sensor 76 is covered with the inflatable rubber bag 70 having a high heat-insulating property, the sensor 76 can measure a temperature of not a surface but a deep portion of a limb. The temperature sensor 78 is used to measure a temperature of ambient air, i.e., a room temperature in a state in which the inflatable rubber bag 70 having the high heat-insulating property is interposed between the subject's portion and the sensor 78. Each of the temperature sensors 76, 78 may be provided by a well-known temperature sensor, such as a thermistor, a semiconductor temperature sensor, a resistance thermometer bulb, or a thermcouple. The upper-arm cuff 40 has a construction similar to that shown in FIG. 2, i.e., supports, on an inside surface thereof, a temperature sensor 80 to measure a temperature of the upper arm 14; and supports, on an outside surface thereof, a temperature sensor 82 to measure a temperature of the ambient air. Respective signals supplied from the temperature sensors 76, 78 are inputted to the control device 36 via an A/D converter 84; and respective signals supplied from the temperature sensors 80, 82 are inputted to the control device 36 via an A/D converter 86. One of the respective temperatures sensors 78, 82 provided on the respective outside surfaces of the ankle cuff 20 and the upper-arm cuff 40 may be omitted.

Figure 3:
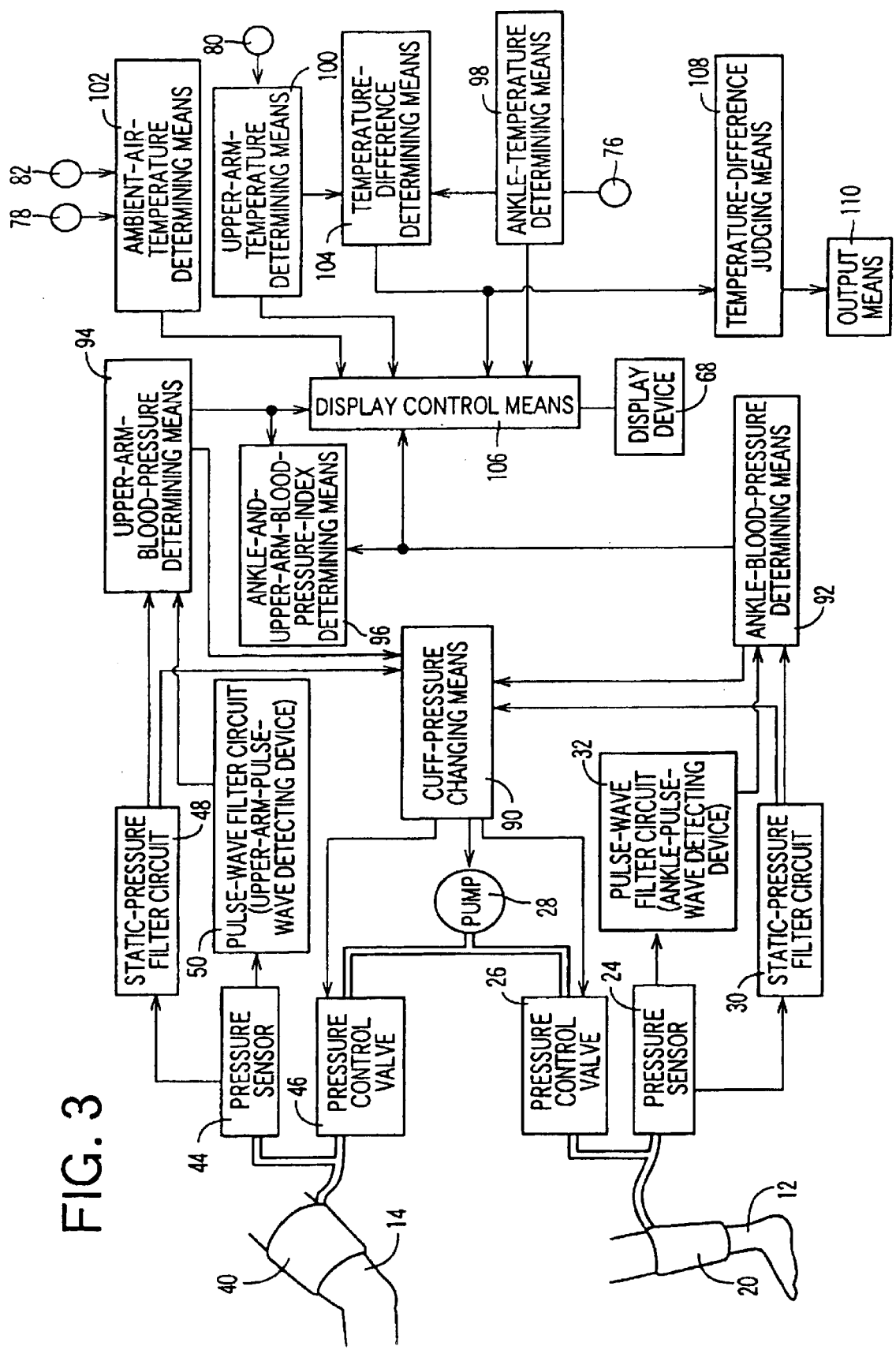
FIG. 3 is a diagrammatic view for explaining essential control functions of an electronic control device of the apparatus of FIG. 1.

FIG. 3 is a diagrammatic view for explaining essential control functions of the electronic control device 36. A cuff-pressure changing means 90 is operated according to a command signal supplied from an ankle-blood-pressure determining means 92 or an upper-arm-blood-pressure determining means 94, both described later, so as to control the air pump 28 and the two pressure control valves 26, 46 connected to the pump 28, based on the ankle-cuff-pressure signal $SC_A$ and the upper-arm-cuff-pressure signal $SC_B$ supplied from the static-pressure filter circuits 30, 48, and thereby control the ankle cuff pressure $PC_A$ and the upper-arm cuff pressure $PC_B$ as follows: First, the ankle cuff pressure $PC_A$ is quickly increased to a pre-set first target pressure $PC_{M1}$ (e.g., 240 mmHg) and the upper-arm cuff pressure $PC_B$ is quickly increased to a pre-set second target pressure (e.g., 180 mmHg). Then, the ankle cuff pressure $PC_A$ and the upper-arm cuff pressure $PC_B$ are slowly decreased at a rate of, e.g., 3 mmHg/sec. In addition, after an ankle diastolic blood-pressure value $BP(A)_{DIA}$ is determined, the ankle cuff pressure $PC_A$ is decreased to an atmospheric pressure; and, after an upper-arm diastolic blood-pressure value $BP(B)_{DIA}$ is determined, the upper-arm cuff pressure $PC_B$ is decreased to the atmospheric pressure. In addition, the cuff-pressure changing means 90 is operated, when pulse waves are detected to measure a pulse-wave propagation velocity, so as to control the air pump 28 and the two pressure control valves 26, 46 connected to the pump 28, and thereby change, and keep, the ankle cuff pressure $PC_A$ and the upper-arm cuff pressure $PC_B$ to, and at, respective pre-set pulse-wave detecting pressures.

The ankle-blood-pressure determining means 92 determines, according to a well-known oscillometric algorithm, a systolic blood-pressure value $BP(A)_{SYS}$, a diastolic blood-pressure value $BP(A)_{DIA}$, and a mean blood-pressure value $BP(A)_{MEAN}$ of the ankle 12, based on respective amplitudes of successive heartbeat-synchronous pulses of the ankle pulse wave continuously detected during the slow decreasing of the ankle cuff pressure $PC_A$ under the control of the cuff pressure changing means 90. A display-control means 106 operates the display device 68 to display the thus determined systolic blood-pressure value $BP(A)_{SYS}$, diastolic blood-pressure value $BP(A)_{DIA}$, and mean blood-pressure value $BP(A)_{MEAN}$. Likewise, the upper-arm-blood-pressure determining means 94 determines, according to the oscillometric algorithm, a systolic blood-pressure value $BP(E)_{SYS}$, a diastolic blood-pressure value $BP(B)_{DIA}$, and a mean blood-pressure value $BP(B)_{MEAN}$ of the upper arm 14, based on respective amplitudes of successive heartbeat-synchronous pulses of the upper-arm pulse wave continuously detected during the slow decreasing of the upper-arm cuff pressure $PC_B$ under the control of the cuff pressure changing means 90. The display-control means 106 operates the display device 68 to display the thus determined systolic blood-pressure value $BP(B)_{SYS}$, diastolic blood-pressure value $BP(B)_{DIA}$, and mean blood pressure value $BP(B)_{MEAN}$.

An ankle-and-upper-arm blood-pressure-index determining means 96 determines an ankle-and-upper-arm blood-pressure index ABI, based on one of the ankle blood-pressure values BP(A) determined by the ankle-blood-pressure determining means 92 and a corresponding one of the upper-arm blood-pressure values BP(B) determined by the upper-arm-blood-pressure determining means 94, and operates the display device 68 to display the thus determined index ABI. Here, for example, the ankle systolic blood-pressure value BP(A) corresponds to the upper-arm systolic blood-pressure value BP(B). In addition, the index ABI may be a value (BP(A)/BP(B)) calculated by dividing the ankle blood-pressure value BP(A) by the upper-arm blood-pressure value BP(B), or a value (BP(B)/BP(A)) calculated by dividing the upper-arm blood-pressure value BP(B) by the ankle blood-pressure value BP(A).

An ankle-temperature determining means 98 determines a temperature T(A) of the ankle 12 around which the ankle cuff 20 is wound, based on the signal supplied from the temperature sensor 76 provided on the inside surface of the ankle cuff 20. An upper-arm-temperature determining means 100 determines a temperature T(B) of the upper arm 14 around which the upper-arm cuff 40 is wound, based on the signal supplied from the temperature sensor 80 provided on the inside surface of the upper-arm cuff 40. An ambient-temperature determining means 102 determines a temperature of the ambient air, i.e., a room temperature T(R), based on the signal or signals supplied from the temperature sensor 28 provided on the outside surface of the ankle cuff 20 and/or the temperature sensor 82 provided on the outside surface of the upper-arm cuff 40. The display-control means 106 operates the display device 68 to display the thus determined ankle temperature T(A), upper-arm temperature T(B), and room temperature T(R).

A temperature-difference determining means 104 determines a temperature difference $\Delta T_{BA}$ (=T(B)−T(A)) between the upper-arm temperature T(B) determined by the upper-arm-temperature determining means 100 and the ankle temperature T(A) determined by the ankle-temperature determining means 98. In addition, the temperature-difference determining means 104 determines a temperature difference $\Delta T_{RA}$ (=T(R)−T(A)) between the room temperature T(R)

determined by the ambient-air-temperature determining means 102 and the ankle temperature T(A) determined by the ankle-temperature determining means 98, and additionally determines a temperature difference $\Delta T_{RB}$ (=T(R)–T(B)) between the room temperature T(R) determined by the ambient-air-temperature determining means 102 and the upper-arm temperature T(B) determined by the upper-arm-temperature determining means 100. The display-control means 106 operates the display device 68 to display the thus determined superior-and-inferior-limb temperature difference $\Delta T_{BA}$, room-and-inferior-limb temperature difference $\Delta T_{RA}$, and room-and-superior-limb temperature difference $\Delta T_{RB}$.

A temperature-difference judging means 108 judges whether the superior-and-inferior-limb temperature difference $\Delta T_{BA}$ (=T(B)–T(A)) determined by the temperature-difference determining means 104 is greater than a pre-set reference value $\Delta T_1$ around an upper limit of a normal range. The reference value $\Delta T_1$ is pre-set at an upper limit of a range in which a change of ankle blood pressure caused by lowering of ankle temperature is negligible. When the temperature-difference judging means 108 judges that the superior-and-inferior-limb temperature difference $\Delta T_{BA}$ is greater than the pre-set reference value $\Delta T_1$, an output means 110 operates the display device 68 to output information indicating the result of judgment, e.g., produce sound or voice, display a message, flicker light, etc., so that the operator is informed of the result. In addition, the temperature-difference judging means 108 judges whether the room-and-inferior-limb temperature difference $\Delta T_{RA}$ and/or the room-and-superior-limb temperature difference $\Delta T_{RB}$ determined by the temperature-difference determining means 104 is greater than a pre-set reference value $\Delta T_2$ around an upper limit of a normal range. The reference value $\Delta T_2$ is pre-set at an upper limit of a range in which a change of limb blood pressure caused by lowering of limb temperature is negligible. When the temperature-difference judging means 108 judges that the room-and-inferior-limb temperature difference $\Delta T_{RA}$ and/or the room-and-superior-limb temperature difference $\Delta T_{RB}$ is greater than the pre-set reference value $\Delta T_2$, the output means 110 operates the display device 68 to output information indicating the result of judgment, e.g., produce sound or voice, display a message, flicker light, etc., so that the operator is informed of the result.

Figure 4:
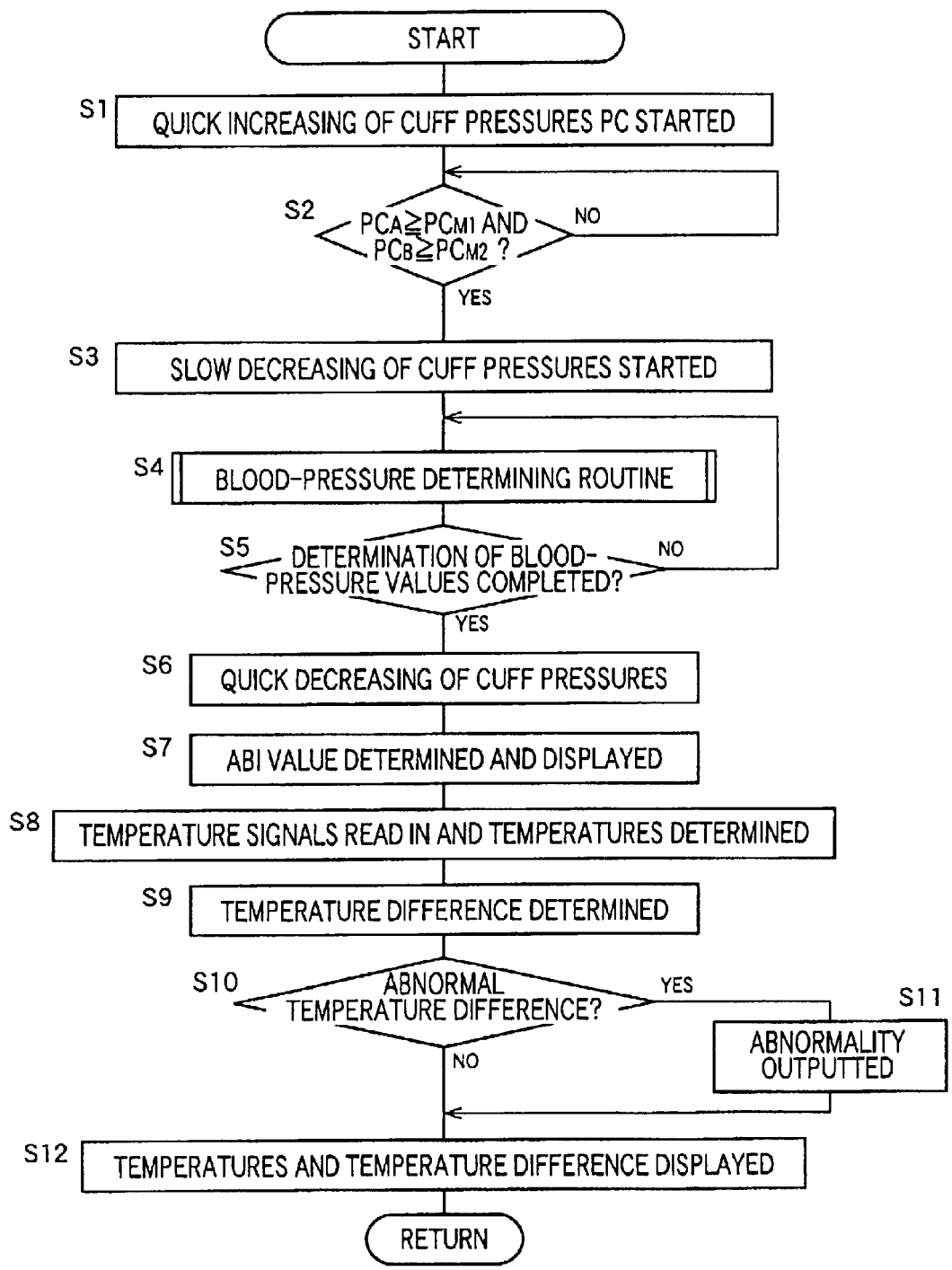
FIG. 4 is a flow chart representing the essential control functions of the electronic control device, shown in FIG. 2.

FIG. 4 is a flow chart representing the essential control functions of the electronic control device 36, shown in FIG. 3, in particular, the control function of measuring respective temperatures of four limbs of a living subject when a blood-pressure measuring operation is carried out to determine an inferior-and-superior-limb blood-pressure index of the subject. The flow chart is carried out each time the control device 36 judges, at a step, not shown, that a starting condition, e.g., operation of a start button, has been satisfied.

In FIG. 4, first, at Step S1 (hereinafter, "Step(s)" is omitted, if appropriate), the control device drives the air pump 28, operates the pressure control valve 26 to start quickly increasing the ankle cuff pressure $PC_A$, and operates the pressure control valve 46 to start quickly increasing the upper-arm cuff pressure $PC_B$. Subsequently, at S2, the control device judges whether the ankle cuff pressure $PC_A$ and the upper-arm cuff pressure $PC_B$ have become equal to, or higher than, the respective target pressure values $PC_{M1}$, $PC_{M2}$. If a negative judgment is made at S2, the control device repeats this step. Meanwhile, if a positive judgment is made at S2, the control goes to S3 to stop the air pump 28 and operate the pressure control valves 26, 46 so as to slowly decrease the ankle cuff pressure $PC_A$ and the upper-arm cuff pressure $PC_B$, each at, e.g., a rate of 3 mmHg/sec. Steps S1 to S3 and S6 correspond to the cuff-pressure changing means 90.

Then, the control goes to S4 corresponding to the ankle-blood-pressure determining means 92 and the upper-arm-blood-pressure determining means 94, i.e., a blood-pressure determining routine. More specifically described, the control device determines respective amplitudes of successive heartbeat-synchronous pulses of the ankle pulse wave represented by the ankle-pulse-wave signal $SM_A$ continuously supplied from the pulse-wave filter circuit 32, and determines, according to a well-known oscillometric blood-pressure-determining algorithm, an ankle systolic blood-pressure value $BP(A)_{SYS}$, an ankle mean blood-pressure value $BP(A)_{MEAN}$, and an ankle diastolic blood-pressure value $BP(A)_{DIA}$, based on the change of the thus determined amplitudes. Similarly, the control device determines respective amplitudes of successive heartbeat-synchronous pulses of the upper-arm pulse wave represented by the upper-arm-pulse-wave signal $SM_B$ continuously supplied from the pulse-wave filter circuit 50, and determines, according to the oscillometric algorithm, an upper-arm systolic blood-pressure value $BP(B)_{SYS}$, an upper-arm mean blood-pressure value $BP(B)_{MEAN}$, and an upper-arm diastolic blood-pressure value $BP(B)_{DIA}$, based on the change of the thus determined amplitudes. Then, at S5, the control device judges whether the determination of blood-pressure values has completed. If a negative judgment is made at S5, the control device repeats S4 and the following steps. Meanwhile, if a positive judgment is made at S5, the control goes to S6 to operate the pressure control valves 26, 46 so as to decrease the cuff pressures $PC_A$, $PC_B$ each to an atmospheric pressure.

Subsequently, the control goes to S7 corresponding to the ankle-and-upper-arm (inferior-and-superior-limb) blood-pressure-index determining means 96 and the display control means 106. At S7, the control device divides the ankle systolic blood-pressure value $BP(A)_{SYS}$ determined at S4, by the upper-arm systolic blood-pressure value $BP(B)_{SYS}$ also determined at S4, thereby determining an index ABI, and operates the display device 68 to display the thus determined index ABI.

Next, the control goes to S8 corresponding to the ankle (inferior-limb) temperature determining means 98, the upper-arm (superior-limb) temperature determining means 100, and the ambient-air-temperature determining means 102. In the state in which the cuffs 20, 40 are worn, the control device reads in the respective signals supplied from the temperature sensors 76, 78, 80, 82, and determines, based on the thus read-in signals, a temperature T(A) of the ankle 12 around which the cuff 20 is wound, a temperature T(B) of the upper arm 14 around which the cuff 40 is wound, and a temperature T(R) of the room temperature.

Then, the control goes to S9 corresponding to the temperature-difference determining means 104. At S9, the control device determines a superior-an-inferior-limb temperature difference $\Delta T_{BA}$ (=T(B)–T(A)) between the upper-arm temperature T(B) and the ankle temperature T(A), each determined at S8, a room-and-inferior-limb temperature difference $\Delta T_{RA}$ (=T(R)–T(A)) between the room temperature T(R) and the ankle temperature T(A), each determined at S8, and a room-and-superior-limb temperature difference $\Delta T_{RB}$ (=T(R)–T(B)) between the room temperature T(R) and the upper-arm temperature T(B), each determined at S8.

Next, the control goes to the temperature-difference judging means 108. At S10, the control device judges whether the superior-and-inferior-limb temperature difference $\Delta T_{BA}$ (=T(B)–T(A)) determined at S9 is greater than a reference value $\Delta T_1$ pre-set around an upper limit of a normal range, and additionally judges whether the room-and-inferior-limb temperature difference $\Delta T_{RA}$ and/or the room-and-superior-limb temperature difference $\Delta T_{RB}$ determined at S9 is greater than a reference value $\Delta T_2$ pre-set around an upper limit of a normal range. If the control device makes two positive judgments, or one positive judgment and one negative judgment, the control goes to S11 corresponding to the output means 110. At S11, when the control device judges that the superior-and-inferior-limb temperature difference $\Delta T_{BA}$ is greater than the pre-set reference value $\Delta T_1$, the control device operates the display device 68 to output information indicating the result of judgment, e.g., produce sound or voice, display a message, flicker a lamp, etc., so that the operator is informed of the result. In addition, when the control device judges that the room-and-inferior-limb temperature difference $\Delta T_{RA}$ and/or the room-and-superior-limb temperature difference $\Delta T_{RB}$ is greater than the pre-set reference value $\Delta T_2$, the control device operates the display device 68 to output information indicating the result of judgment, e.g., produce sound or voice, display a message, flicker a lamp, etc., so that the operator is informed of the result. Then, the control goes to S12 corresponding to the display control means 106. At S12, the control device operates the display device 68 to display the ankle temperature T(A), the upper-arm temperature T(B), and the room temperature T(R), each determined at S8, and the superior-and-inferior-limb temperature difference $\Delta T_{BA}$, the room-and-inferior-limb temperature difference $\Delta T_{RA}$, and the room-and-superior-limb temperature difference $\Delta T_{RB}$, each determined at S9.

As is apparent from the foregoing description of the present embodiment, the temperature sensor 76, 80 is provided in the inside surface of the ankle cuff 20 or the upper-arm cuff 40 wound around the ankle 12 or the upper arm 14 as a portion of a living subject, and the ankle temperature T(A) or the upper-arm temperature T(B) detected by the temperature sensor 76, 80 is displayed by the display device 68. Thus, an operator such as a doctor can recognize the temperature of the ankle 12 or the upper arm 14 around which the ankle cuff 20 or the upper-arm cuff 40 is wound to measure a blood pressure of the ankle 12 or the arm 14, and accordingly can easily judge whether the measured blood pressure of the ankle 12 or the arm 14 is reliable. If the temperature of the ankle 12 or the arm 14 displayed by the display device 68 falls within a predetermined normal range, the operator can judge that the measured blood pressure is not lowered by the influence of the body temperature. On the other hand, if the temperature of the ankle 12 or the arm 14 displayed by the display device 68 does not fall within the normal range, the operator can again operate the present apparatus to obtain a reliable blood-pressure value of the subject.

In the present embodiment, the temperature sensor 78, 82 is additionally provided in the outside surface of the ankle cuff 20 or the upper-arm cuff 40 to detect the temperature of the ambient air, and the display device 68 additionally displays the ambient-air temperature detected by the temperature sensor 78, 82. Therefore, if the temperature(s) of the ankle 12 or/and the upper arm 14 is/are low, the operator can easily judge whether the temperature(s) of the ankle 12 or/and the upper arm 14 is/are lowered by the ambient air, e.g., room temperature.

In the present embodiment, the temperature-difference determining means 104 (S9) determines the room-and-inferior-limb temperature difference $\Delta T_{RA}$ between the temperature of the ankle 12 detected by the temperature sensor 76 and the temperature of the ambient air detected by the temperature sensor 78, and the room-and-superior-limb temperature difference $\Delta T_{RB}$ between the temperature of the upper arm 14 detected by the temperature sensor 80 and the temperature of the ambient air detected by the temperature sensor 82, and the display device 68 additionally displays the room-and-inferior-limb temperature difference $\Delta T_{RA}$ and the room-and-superior-limb temperature difference $\Delta T_{RB}$ determined by the temperature-difference determining means 104. Accordingly, the operator can easily recognize the temperature difference between the temperature of the ankle 12 or the upper arm 14 around which the ankle cuff 20 or the upper-arm cuff 40 is wound and the temperature of the ambient air. Therefore, if the temperature of the ankle 12 or the arm 14 is low, the operator can easily take a treatment or an action against the low temperature. More specifically described, if the temperature of the ankle 12 or the arm 14 is low and the above-indicated temperature difference is considerably small, the operator can raise the room temperature; and if the temperature of the ankle 12 or the arm 14 is low and the temperature difference is considerably large, the operator can positively raise the temperature of the portion of the subject by wearing a cloth on the portion or giving a massage to the portion.

Also, in the present embodiment, the temperature-difference judging means 108 (S10) judges whether the temperature difference determined by the temperature-difference determining means 104 (S9) is greater than a pre-set reference value, and the output means 110 (S11) operates for outputting information indicating the judgment made by the judging means 108. The output means 110 operates for outputting the information, such as a message in the form of a sound or voice, or an image, or a printed matter. From the information, the operator can easily recognize the temperature difference between the temperature of the ankle 12 or the upper arm 14 around which the ankle cuff 20 or the upper-arm cuff 40 is wound and the temperature of the ambient air. Therefore, if the temperature of the portion of the subject is low, the operator can easily take an appropriate treatment or action against the low temperature.

In addition, in the present embodiment, the display control means 106 (S12) controls the display device 68 to simultaneously display the temperature T(A) of the ankle (the inferior limb) measured by the temperature sensor (the inferior-limb temperature measuring device) 76 and the temperature T(B) of the upper arm (the superior limb) measured by the temperature sensor (the superior-limb temperature measuring device) 80. Since the operator can recognize the respective temperatures T(A), T(B) of the ankle and the upper arm around which the ankle and upper-arm cuffs 20, 40 are wound in the blood-pressure measurement, the operator can easily judge whether the upper-arm systolic, diastolic, and mean blood-pressure values $BP(B)_{SYS}$, $BP(B)_{DIA}$, $BP(B)_{MEAN}$ and the ankle systolic, diastolic, and mean blood-pressure values $BP(A)_{SYS}$, $BP(A)_{DIA}$, $BP(A)_{MEAN}$, measured by the upper-arm (superior-limb) blood-pressure measuring device 18 and the ankle (inferior-limb) blood-pressure measuring device 16, are reliable. For example, if the temperature T(A) of the inferior limb is much lower than that T(B) of the superior limb, the operator can judge that the accuracy of the blood-pressure values of the inferior limb, that is, the ankle systolic, diastolic, and mean blood-pressure values $BP(A)_{SYS}$, $BP(A)_{DIA}$, $BP(A)_{MEAN}$ is low because of the influence of the low temperature T(A) of the inferior limb. In this case, the operator can try to measure a reliable blood-pressure value after raising the temperature of the inferior limb.

In addition, in the present embodiment, if the superior-and-inferior-limb temperature difference $\Delta T_{BA}$ between the respective temperatures T(A), T(B) of the ankle (the inferior limb) and the upper arm (the superior limb), determined by the temperature-difference determining means 104 (S9), is greater than the pre-set reference value $\Delta T_1$, the output means 110 (S11) operates for outputting information related to thee fact that the superior-and-inferior-limb temperature difference $\Delta T_{BA}$ is greater than the pre-set reference value $\Delta T_1$. Thus, the operator can easily judge whether the respective blood-pressure values measured by the upper-arm (superior-limb) blood-pressure measuring device 18 and the ankle (inferior-limb) blood-pressure measuring device 16 are reliable. For example, if the temperature T(A) of the ankle (the inferior limb) is much lower than that T(B) of the upper arm (the superior limb), the operator can judge that the accuracy of the blood-pressure values of the inferior limb, that is, the ankle systolic, diastolic, and mean blood-pressure values $BP(A)_{SYS}$, $BP(A)_{DIA}$, $BP(A)_{MEAN}$ is low because of the influence of the low temperature of the inferior limb. In this case, the operator can try to measure a reliable blood-pressure value after raising the temperature of the inferior limb.

Also, in the present embodiment, the inferior-limb temperature measuring device includes the temperature sensor 76 which is provided in the inside surface of the ankle cuff 20 adapted to be wound around the inferior limb of the living subject and is adapted to contact the skin of the ankle 12, and the temperature sensor 78 is provided in the outside surface of the ankle cuff 20 so as to detect the temperature of the ambient air. Accordingly, when the ankle cuff 20 is worn on the ankle 12, the temperature sensor 76 to detect the temperature of the ankle 12 and the temperature sensor 78 to detect the temperature of the ambient air are simultaneously worn on the ankle 12.

In addition, in the present embodiment, the superior-limb temperature measuring device includes the temperature sensor 80 which is provided in the inside surface of the upper-arm cuff 40 adapted to be wound around the superior limb of the subject and is adapted to contact the skin of the upper arm 14. Accordingly, when the upper-arm cuff 40 is worn on the upper arm 14, the temperature sensor 80 to detect the temperature of the arm 14 is also worn on the arm 14.

While the present invention has been described in its preferred embodiment by reference to the drawings, it is to be understood that the present invention may otherwise be embodied.

For example, in the illustrated embodiment, the ankle cuff 20 adapted to be wound around the ankle 12 is used as the cuff adapted to be wound around the inferior limb of the living subject. However, it is possible to employ a cuff adapted to be wound around a femoral portion of a living subject. In addition, while in the illustrated embodiment the upper-arm cuff 40 adapted to be wound around the upper arm 14 is used as the cuff adapted to be wound around the superior limb of the living subject, it is possible to employ a cuff adapted to be wound around a wrist or a finger of a living subject.

Also, in the illustrated embodiment, the temperature sensor 76 employed to measure the temperature of the inferior limb is provided in the inside surface of the ankle cuff 20. However, it is possible to wear the temperature sensor 76 independent of the ankle cuff 20. Likewise, while in the illustrated embodiment the temperature sensor 80 employed to measure the temperature of the superior limb is provided in the inside surface of the upper-arm cuff 40, it is possible to wear the temperature sensor 80 independent of the upper-arm cuff 40.

It is to be understood that the present invention may be embodied with other changes, improvements and modifications that may occur to a person skilled in the art without departing from the spirit and scope of the invention defined in the appended claims.

What is claimed is:

1. An apparatus for measuring a blood pressure of a living subject, comprising:

an inflatable cuff which has an inside surface adapted to contact a body surface of the subject and an outside surface exposed to an ambient air, and which is adapted to be wound around a portion of the subject to press the portion of the subject;

a first temperature sensor which is provided in the outside surface of the cuff and detects, in a state in which the cuff is wound around the portion of the subject, a temperature of the portion of the subject;

a second temperature sensor which is provided in the outside surface of the cuff and detects, in the state in which the cuff is wound around the portion of the subject, a temperature of the ambient air;

a temperature-difference determining means for determining a difference between the temperature of the portion of the subject detected by the first temperature sensor and the temperature of the ambient air detected by the second temperature sensor, and a display device which displays the temperature of the portion of the subject, detected by the first temperature sensor, the temperature of the ambient air, detected by the second temperature sensor, and the temperature difference determined by the temperature-difference determining means.

2. An apparatus for measuring a blood pressure of a living subject, comprising:

an inflatable cuff which has an inside surface adapted to contact a body surface of the subject and an outside surface exposed to an ambient air, and which is adapted to be wound around a portion of the subject to press the portion of the subject;

a first temperature sensor which is provided in the inside surface of the cuff and detects, in a state in which the cuff is wound around the portion of the subject, a temperature of the portion of the subject;

a second temperature sensor which is provided in the outside surface of the cuff and detects, in the state in which the cuff is wound around the portion of the subject, a temperature of the ambient air;

a temperature-difference determining mean for determining a difference between the temperature of the portion of the subject detected by the first temperature sensor and the temperature of the ambient air detected by the second temperature sensor;

a judging means for judging whether the temperature difference determined by the temperature-difference determining means is greater than a reference value; and an output device which outputs information indicating a judgment made by the judging means.

3. An apparatus for measuring an inferior-and-superior-limb blood-pressure index of living subject, comprising:

an inferior-limb blood-pressure measuring device which includes an inferior-limb cuff adapted to be wound around an inferiority of the subject and measures a blood pressure of the inferior limb;

a superior-limb blood-pressure measuring device which includes a superior-limb cuff adapted to be wound around a superior limb of the subject and measures a blood pressure of the superior limb;

an inferior-and-superior-limb blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device;

a display device which displays the inferior-and-superior-limb blood-pressure index of the subject determined by the inferior-and-superior-limb blood-pressure-index determining means;

an inferior-limb temperature measuring device which measures a temperature of the inferior limb of the subject;

a superior-limb temperature measuring device which measures temperature of the superior limb of the subject; and a display control means for controlling the display device to simultaneously display the temperature of the inferior limb of the subject measured by the inferior-limb temperature measuring device and the temperature of the superior limb of the subject measured by the superior-limb temperature measuring device.

4. An apparatus according to claim 3, wherein the inferior-limb temperature measuring device comprises an inferior-limb temperature sensor which is provided in an inside surface of the inferior-limb cuff and is adapted to contact skin of the inferior limb of the subject so as to measure the temperature of the inferior limb of the subject.

5. An apparatus according to claim 4, further comprising an ambient-air temperature sensor which is provided in an outside surface of the inferior-limb cuff and detects, in the state in which the inferior-limb cuff is wound around the inferior-limb of the subject, a temperature of the ambient air.

6. An apparatus according to claim 3, wherein the superior-limb temperature measuring device comprises a superior-limb temperature sensor which is provided in an inside surface of the superior-limb cuff and is adapted to contact a skin of the superior limb of the subject so as to measure the temperature of the superior limb of the subject.

7. An apparatus for measuring an inferior-and-superior-limb blood-pressure index of living subject, comprising:

an inferior-limb blood-pressure measuring device which include an inferior-limb cuff adapted to be wound around an inferior limb of the subject and measures a blood pressure of the inferior limb;

a superior-limb blood-pressure measuring device which includes a superior-limb cuff adapted to be wound around a superior limb of the subject and measures a blood pressure of the superior limb;

an inferior-and-superior-limb blood-pressure-index determining means for determining the inferior-and-superior-limb blood-pressure index of the subject, based on the blood pressure of the inferior limb measured by the inferior-limb blood-pressure measuring device and the blood pressure of the superior limb measured by the superior-limb blood-pressure measuring device;

a display device which displays the inferior-and-superior-limb blood-pressure index of the subject determined by the inferior-and-superior-limb blood-pressure-index determining means;

an inferior-limb temperature measuring device which measures a temperature of the inferior limb of the subject;

a superior-limb temperature measuring device which measures temperature of the superior limb of the subject;

a temperature-difference determining means for determining a difference between the temperature of the inferior limb of the subject measured by the inferior-limb temperature measuring device and the temperature of the superior limb of the subject measured by the superior-limb temperature measuring device; and an output device which outputs, when the temperature difference determined by the temperature-difference determining means is greater than a reference value, information related to a fact that the temperature difference is greater than the reference value.

\* \* \* \* \*